US009536346B2

(12) United States Patent
Sakuragi (10) Patent No.: US 9,536,346 B2
(45) Date of Patent: Jan. 3, 2017

(54) MEDICAL IMAGE DISPLAY APPARATUS, MEDICAL IMAGE DISPLAY METHOD, AND MEDICAL IMAGE DISPLAY PROGRAM

(71) Applicant: FUJIFILM Corporation, Tokyo (JP)

(72) Inventor: Futoshi Sakuragi, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 14/484,072

(22) Filed: Sep. 11, 2014

(65) Prior Publication Data

US 2014/0375632 A1 Dec. 25, 2014

Related U.S. Application Data

(63) Continuation of application No. PCT/JP2013/001643, filed on Mar. 13, 2013.

(30) Foreign Application Priority Data

Mar. 15, 2012 (JP) .................................. 2012-058254

(51) Int. Cl.
G06T 15/00 (2011.01)
G06T 15/08 (2011.01)
(Continued)

(52) U.S. Cl.
CPC ............... *G06T 15/08* (2013.01); *A61B 5/743* (2013.01); *A61B 6/466* (2013.01); *A61B 6/504* (2013.01);
(Continued)

(58) Field of Classification Search
None
See application file for complete search history.

(56) References Cited

U.S. PATENT DOCUMENTS

2002/0035330 A1 3/2002 Cline et al.
2003/0095147 A1* 5/2003 Daw .............................. 345/771
(Continued)

FOREIGN PATENT DOCUMENTS

CN 101160104 A 4/2008
CN 102246206 A 11/2011
(Continued)

OTHER PUBLICATIONS

Fabrice et al. (WO2012085163A1 ).*
(Continued)

*Primary Examiner* — Kyle Zhai
(74) *Attorney, Agent, or Firm* — McGinn IP Law Group, PLLC.

(57) ABSTRACT

A medical image display apparatus includes: a medical image obtaining section for obtaining a three dimensional medical image of a subject; a display control section for displaying the three dimensional medical image obtained by the medical image obtaining section and an additional information image that represents information added to the three dimensional medical image; and an additional information display command receiving section for receiving a command to display the additional information image along with the three dimensional medical image. The display control section displays the additional information image along with the three dimensional medical image and changing the color of the displayed three dimensional medical image to a color which can be discriminated from the color of the additional information image, when the command to display the additional information image is received.

15 Claims, 5 Drawing Sheets

(51) Int. Cl.

| | | |
|---|---|---|
| *A61B 5/00* | (2006.01) | |
| *A61B 6/00* | (2006.01) | |
| *G06F 19/00* | (2011.01) | |
| *G06T 19/20* | (2011.01) | |
| *A61B 5/055* | (2006.01) | |
| *A61B 6/03* | (2006.01) | |

(52) U.S. Cl.
CPC ............ *G06F 19/321* (2013.01); *G06T 19/20* (2013.01); *A61B 5/055* (2013.01); *A61B 5/748* (2013.01); *A61B 6/032* (2013.01); *G06T 2210/41* (2013.01); *G06T 2219/2012* (2013.01)

(56) References Cited

U.S. PATENT DOCUMENTS

| | | | |
|---|---|---|---|
| 2005/0065406 A1 | 3/2005 | Cline et al. | |
| 2006/0044324 A1* | 3/2006 | Shum .................... | G06T 11/001 345/595 |
| 2006/0108509 A1 | 5/2006 | Frangioni et al. | |
| 2006/0177133 A1 | 8/2006 | Kee | |
| 2007/0167801 A1 | 7/2007 | Webler et al. | |
| 2008/0228037 A1 | 9/2008 | Cline et al. | |
| 2008/0240535 A1 | 10/2008 | Frangioni et al. | |
| 2009/0016483 A1 | 1/2009 | Kawasaki et al. | |
| 2009/0310846 A1* | 12/2009 | Lemchen .............. | G06T 19/003 382/132 |
| 2010/0198010 A1 | 8/2010 | Cline et al. | |
| 2010/0210904 A1 | 8/2010 | Cline et al. | |
| 2010/0220742 A1 | 9/2010 | Brewer et al. | |
| 2011/0235891 A1 | 9/2011 | Sonnemans et al. | |
| 2012/0026162 A1 | 2/2012 | Masumoto | |
| 2015/0230698 A1 | 8/2015 | Cline et al. | |

FOREIGN PATENT DOCUMENTS

| | | |
|---|---|---|
| JP | H 03-33986 A | 2/1991 |
| JP | H 07-213522 A | 8/1995 |
| JP | 2001-149366 A | 6/2001 |
| JP | 2001-283191 A | 10/2001 |
| JP | 2003-265416 A | 9/2003 |
| JP | 2004-089599 A | 3/2004 |
| JP | 2005-103053 A | 4/2005 |
| JP | 2008-521462 A | 6/2008 |
| JP | 2008-245832 A | 10/2008 |
| JP | 2010-131315 A | 6/2010 |
| JP | 2010/220742 A | 10/2010 |
| JP | 4717935 B2 | 7/2011 |
| JP | 2012-024517 A | 2/2012 |
| WO | WO 2010/067276 A1 | 6/2010 |

OTHER PUBLICATIONS

International Search Report (ISR) (PCT Form PCT/ISA/210), in PCT/JP2013/001643, dated Jun. 11, 2013.
Japanese Office Action dated Jun. 30, 2015 with an English translation thereof.
Extended European Search Report dated Mar. 22, 2016.
Chinese Office Action dated Feb. 14, 2016 with a partial English translation.
Japanese Office Action dated Mar. 15, 2016 with an English translation.
Chinese Office Action dated Oct. 10, 2016, with an English translation thereof.

* cited by examiner

FIG.3

THREE DIMENSIONAL MEDICAL IMAGE 5
(COLOR DISPLAY: LIGHT GREEN)

FIG.4

SURFACE IMAGE OF CUT CROSS SECTION
(COLOR DISPLAY: DARK GREEN)

THREE DIMENSIONAL MEDICAL IMAGE 5
(COLOR DISPLAY: LIGHT GREEN)

MEDICAL IMAGE DISPLAY APPARATUS, MEDICAL IMAGE DISPLAY METHOD, AND MEDICAL IMAGE DISPLAY PROGRAM

CROSS REFERENCE TO RELATED APPLICATIONS

The present application is a Continuation of PCT International Application No. PCT/JP2013/001643 filed on Mar. 13, 2013, which claims priority under 35 USC §119 (a) to Japanese Patent Application No. 2012-058254 filed on Mar. 15, 2012. Each of the above application (s) is hereby expressly incorporated by reference in its entirety, into the present application.

TECHNICAL FIELD

The present invention is related to a medical image display apparatus, a medical image display method, and a medical image display program. The present invention is particularly related to a that medical image display apparatus, a medical image display method, and a medical image display program that display additional information images that represent information added to three dimensional medical images along with the three dimensional medical images.

BACKGROUND ART

Conventionally, three dimensional medical images of subjects are obtained by imaging the subjects with a CT (Computed Tomography) apparatus, an MRI (Magnetic Resonance Imaging) apparatus, or the like. These three dimensional medical images are displayed to users on display devices by display methods such as MPR (Multi Planar Reconstruction) and volume rendering.

When explanations are given while showing the three dimensional medical images to third parties for reports, at conferences, and at research presentations, arrows that indicate regions of interest within the three dimensional medical images were added as annotations and displayed.

DISCLOSURE OF THE INVENTION

When annotations are added as described above, it is necessary to set the color of the annotations such that they can be distinguished from the color of the three dimensional medical images. However, there were cases in which it is difficult to distinguish the color of the annotations, which are set in advance, from the color of the three dimensional medical images.

In addition, when CPR (Curved Planar Reformation) images are displayed based on three dimensional medical images, there are cases in which the images of cut curved surfaces of the CPR images are displayed on volume rendered images as annotations. Generally, volume rendered images are displayed as color images. Therefore, there are cases in which the images of cut curved surfaces become buried within the volume rendered images depending on the color thereof. In such cases, it will become difficult to understand which curved surface is being displayed. In addition, it is desirable for a color specified by a user to be employed as the color of the annotations, in order to facilitate viewing by third parties or to emphasize the annotations.

Japanese Unexamined Patent Publication No. 2008-245832 proposes to adjust the brightness of an object such as a text box according to the brightness of a medical image when displaying the object along with the medical image. However, the brightness of the object is adjusted in order to solve a problem that medical images, in which high display precision is required, may be influenced depending on the brightness of objects displayed therewith, resulting in image diagnosis being adversely affected. Japanese Unexamined Patent Publication No. 2008-245832 does not propose any measures from the viewpoint of facilitating discrimination of objects.

Japanese Unexamined Patent Publication Nos. 2001-283191 and 2010-131315 propose displaying a region of interest and regions other than the region of interest such that they can be distinguished from each other. However, Japanese Unexamined Patent Publication Nos. 2001-283191 and 2010-131315 are silent regarding the relationship between annotations and three dimensional medical images.

The present invention has been developed in view of the foregoing circumstances. It is an object of the present invention to provide a medical image display apparatus, a medical image display method, and a medical image display program that display a three dimensional medical image of a subject and an additional information image that represents information added to the three dimensional medical image in a desired color which enables the additional information image to be clearly distinguished from the three dimensional medical image.

A medical image display apparatus of the present invention comprises:

medical image obtaining means for obtaining a three dimensional medical image of a subject;

display control means for displaying the three dimensional medical image obtained by the medical image obtaining means and an additional information image that represents information added to the three dimensional medical image; and additional information display command receiving means for receiving a command to display the additional information image along with the three dimensional medical image;

the display control means displaying the additional information image along with the three dimensional medical image and changing the color of the displayed three dimensional medical image to a color which can be discriminated from the color of the additional information image, when the command to display the additional information image is received.

In the medical image display apparatus of the present invention, the display control means may display the additional information image in color, and change the display of the three dimensional medical image from color display to black and white display.

A configuration may be adopted, wherein the medical image display apparatus further comprises:

color change command receiving means for receiving a command to change the color of the additional information image; and wherein:

the display control means changes the color of the displayed three dimensional image to a color which can be discriminated from the color of the additional information image after the color of the additional information image is changed, when the command to change the color of the additional information image is received by the color change command receiving means.

A configuration may be adopted, wherein:
the display control means displays an indicator that indicates a predetermined position within the three dimensional medical image as the additional information image.

A configuration may be adopted, wherein:
the display control means displays a CPR (Curved Planar Reformation) image based on the three dimensional medical image, and displays an image that represents a cut curved surface of the CPR image as the additional information image on the three dimensional medical image.

A configuration may be adopted, wherein:
the additional information display command receiving means also receives a command to not display the additional information image; and
the display control means ceases display of the additional information image and return the color of the three dimensional medical image to the color it had been displayed in prior to being changed, when the command to not display the additional information image is received.

A configuration may be adopted, wherein:
the display control means returns the display of the three dimensional medical image to color display, which is the manner in which the three dimensional medical image is displayed prior to being changed to black and white display, when the command to not display the additional information image is received.

A configuration may be adopted, wherein:
the display control means displays a volume rendered image as the three dimensional medical image.

A medical image display method of the present invention comprises:
obtaining a three dimensional medical image of a subject; and
displaying the three dimensional medical image and an additional information image that represents information added to the three dimensional medical image;
the additional information image being displayed along with the three dimensional medical image and the color of the displayed three dimensional medical image being changed to a color which can be discriminated from the color of the additional information image, when a command to display the additional information image is received.

A medical image display program of the present invention causes a computer to function as:
medical image obtaining means for obtaining a three dimensional medical image of a subject;
display control means for displaying the three dimensional medical image obtained by the medical image obtaining means and an additional information image that represents information added to the three dimensional medical image; and
additional information display command receiving means for receiving a command to display the additional information image along with the three dimensional medical image;
the display control means displaying the additional information image along with the three dimensional medical image and changing the color of the displayed three dimensional medical image to a color which can be discriminated from the color of the additional information image, when the command to display the additional information image is received.

The medical image display apparatus, the medical image display method, and the medical image display program of the present invention receive commands to display additional information images along with three dimensional medical images. In the case that the commands to display the additional information images are received, the additional information images are displayed along with the three dimensional medical images, and the color of the three dimensional medical images which are being displayed is changed to a color which can be discriminated from the color of the additional information images. Therefore, the additional information images can be displayed with a desired color, and the additional information images and the three dimensional medical images can be clearly distinguished from each other.

In addition, a configuration may be adopted, wherein a command to change the color of the additional information image may be received; and the color of the displayed three dimensional image is changed to a color which can be discriminated from the color of the additional information image after the color of the additional information image is changed, when the command to change the color of the additional information image is received by the color change command receiving means. In this case, the color of the additional information image can be changed by a user, while the additional information images and the three dimensional medical images can be clearly distinguished from each other regardless of what color the additional information image is changed into.

Further, a configuration may be adopted, wherein a command to not display the additional information image may be received; and display of the additional information image is ceased and the color of the three dimensional medical image is returned to the color it had been displayed in prior to being changed, when the command to not display the additional information image is received. In this case, the color of the three dimensional medical image can be returned to a color that a user is accustomed to viewing the three dimensional medical image in, in a state in which the additional information image is not being displayed.

BEST MODE FOR CARRYING OUT THE INVENTION

Figure 1:
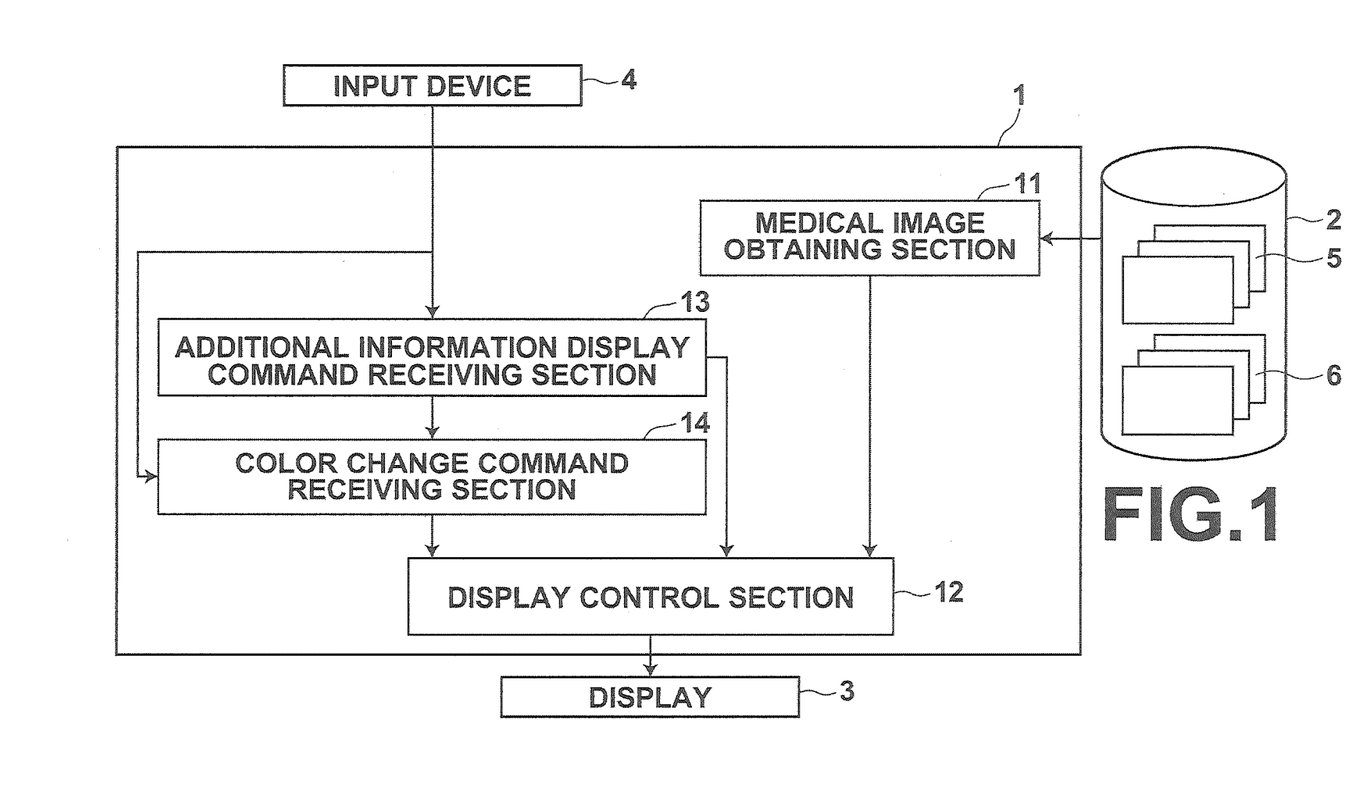
FIG. 1 is a diagram that schematically illustrates the configuration of a medical image display system in which a medical image display apparatus according to an embodiment of the present invention is incorporated.

Hereinafter, a medical image display apparatus, a medical image display program, and a medical image display method according to an embodiment of the present invention will be described in detail with reference to the attached drawings. FIG. 1 is a diagram that schematically illustrates the configuration of a medical image display system in which a medical image display apparatus according to an embodiment of the present invention is incorporated. As illustrated in FIG. 1, the medical image display system according to the present embodiment is equipped with a medical image display apparatus 1, a storage device 2, and a display 3.

The medical image display apparatus 1 is a single computer, in which the medical image display program of the present invention is installed. The computer may be a work station or a personal computer that a physician that performs image diagnosis operates directly. Alternatively, the computer may be a server computer which is connected to the work station or the personal computer via a network. The medical image display program is stored in a recording medium such as a DVD or a CD-ROM, or in a server computer connected to a network to be accessible from the exterior. The medical image display program is read out from the recording medium or the server computer, downloaded into the computer, and installed in response to a request from a physician.

The medical image display apparatus 1 is equipped with a CPU (Central Processing Unit), a semiconductor memory, a storage device such as a hard disk and an SSD (Solid State Drive), in which the medical image display program is installed, etc. These hardware components constitute a medical image obtaining section 11 (medical image obtaining means), a display control section 12 (display control means), an additional information display command receiving section 13 (additional information display command receiving means), and a color change command receiving section 14 (color change command receiving means) as illustrated in FIG. 1. Each of the above sections function by the medical image display program installed in the hard disk being executed by the central processing unit. In addition, the display 3 and input devices 4 constituted by a mouse, a keyboard, and the like, are connected to the medical image display apparatus 1.

The medical image obtaining section 11 obtains three dimensional medical images of subjects, which are photographed in advance. Specifically, the medical image obtaining section 11 obtains three dimensional medical images 5 which are taken of subjects during CT examinations and MRI examinations, as well as CPR (Curved Planar Reformation) images 6 which are generated based on such three dimensional medical images 5. The CPR images 6 are images which are generated by cutting a three dimensional medical image of an elongate structure such as a blood vessel, a bronchial tube, a large intestine, and a spine along a cut curved plane along the centerline of the structure, and then by stretching the curved plane. CPR images may be displayed as three different types of images, which are a projected CPR image, a stretched CPR image, and a straight CPR image, by techniques for displaying two dimensional planar images of the cut plane. Note that the three dimensional medical images 5 and the CPR images 6 are stored in the storage device 2 in advance.

The display control section 12 displays the three dimensional medical images 5 obtained by the medical image obtaining section 11 and the aforementioned CPR images 6 on the display 3. Further, the display control section 12 displays additional information images that represent information which is added to the three dimensional medical images 5.

The additional information images are similar to annotations. Specific examples of the additional information image include: an image that represents the surface of the cut curved plane of the CPR image 6 in the three dimensional medical image 5 (hereinafter, referred to as "surface image of cut curved plane") and an indicator which is displayed to specify the position of a region of interest in a three dimensional medical image 5. Examples of such an indicator include a cursor represented as an arrow or an x, and a square or a circular frame image that indicates the position and range of a region of interest. The additional information images also include images of comment fields in which findings regarding the three dimensional medical images 5 are written. That is, the additional information images may be any type of image as long as they represent information which is added to the three dimensional medical images 5.

Note that the surface images of cut curved planes of the CPR images 6 in the three dimensional medical image 5 are generated based on information which is employed when generating the CPR images 6, such as the core axes of tubular tissue such as blood vessels and bronchial tubes. Such information is input to the medical image display apparatus 1 along with the CPR images 6. The display control section 12 generates the surface images of cut curved planes of the CPR images 6 based on the input information. Methods for generating surface images of cut planes of CPR images 6 are known, as disclosed in Japanese Unexamined Patent Publication No. 2012-024517, for example. Therefore, a detailed description thereof will be omitted here.

In addition, the display control section 12 controls the display and non display of the surface images of cut curved planes of the CPR images 6 (additional information image) and controls color changes as will be described below. At this time, the display control section 12 employs the information of the core axes which is used when generating the CPR image 6. The information regarding the core axes can be obtained by using the method described in Japanese Patent No. 4717935, for example. Hereinbelow, a method for obtaining the information regarding the core axes of the blood vessels of the heart will be described.

Specifically, first, Gaussian pyramids are generated by administering multiple resolution transform on a three dimensional medical image of the heart.

Then, to blood vessel candidates constituted by linear structures having different sizes are detected by administering a predetermined detection process on each of the generated Gaussian pyramids. Next, eigenvalue analysis of Hessian matrices is performed in predetermined regions that include the blood vessel candidates, to calculate the directions of the main axes of the blood vessel candidates. A Hessian matrix is a matrix in which the elements are partial derivatives of the second floor. For a three dimensional image, a Hessian matrix is a 3 by 3 matrix as shown in the formula below.

$$\nabla^2 I = \begin{bmatrix} I_{xx} & I_{xy} & I_{xz} \\ I_{xx} & I_{xy} & I_{xz} \\ I_{xx} & I_{xy} & I_{xz} \end{bmatrix} \quad \text{[Formula 1]}$$

$$I_{xx} = \frac{\delta^2 I}{\delta x^2}, I_{xy} = \frac{\delta^2 I}{\delta x \delta y^2}, \ldots$$

Here, when λ1, λ2, and λ3 are the eigenvalues of the Hessian matrix at an arbitrary pixel and in the case that two of the eigenvalues are large and one of the eigenvalues is close to 0, for example, when λ3, λ2>>λ1 and λ1≈0 are satisfied, it is know that the pixel is that of a linear structure. Therefore, the eigenvector corresponding to the minimum eigenvalue (λ1≈0) of the Hessian matrix is the direction of the main axis of a vessel candidate.

Next, a normalization process is performed on a predetermined target area that includes the blood vessel candidates, based on the direction of the main axis which is calculated in the manner described above. Then, feature quantities are calculated from the normalized target region by a machine learning technique. The calculated feature amounts are employed to judge whether true blood vessels are included in the target region.

In the case that it is judged that a blood vessel is included, a predetermined point within the target region is set as a candidate point. The judgment described above is repeated until there are no more target regions to be judged.

Next, when the judgments of all of the target regions are completed and judgments are no longer required, a cost function is employed to reconstruct whether the plurality of candidate points can be connected, and the core axis of a blood vessel is obtained. The conditions of the cost function with respect to the relationship between at least two of the candidate points from among the plurality of set candidate points are that the two candidate points are within a predetermined distance from each other, based on position information of the candidate points, and that the sum of two acute angles formed by a base line connecting the two candidate points and the directions of the main axes of the two candidate points is less than a predetermined angle. Specifically, for example, the minimum spanning tree method may be employed to reconstruct the plurality of candidate points, to obtain the core axis of the blood vessel. Note that as described above, the core axis of the blood vessel is employed to generate CPR images of the blood vessel and the surface images of the cut curved planes of the CPR images.

The additional information display command receiving section 13 receives a command to display an additional information image or a command to not display an additional information image along with a three dimensional medical image 5 which is being displayed on the display 3, and outputs a signal indicating receipt of the command signal to the display control section 12. The command to display or to not display the additional information image is input by a user using the input devices 4, and the additional information display command receiving section 13 receives signals input from the input devices 4.

When a command signal to display an additional information image is input, the display control section 12 displays the additional information image as described above on the display 3. When a command signal to not display the additional information image is input, the display control section 12 ceases display of the additional information image which is being displayed on the display 3.

Further, when a command signal to display the additional information image is input, the display control section 12 displays the additional information image as described above, and changes the color of the three dimensional medical image 5 that is currently being displayed to that which can be distinguished from the color of the additional information image.

More specifically, for example, in the case that settings which are set in advance specify that the three dimensional medical image 5 is to be displayed in color, and that the additional information image is also to be displayed in color, the display control section 12 displays the additional information image in color when an command signal to display the additional information image is input and changes the display of the three dimensional medical image 5 which is currently being displayed from color display to black and white display.

Note that it is not necessary for the color of the three dimensional medical image 5 after the color change to be black and white as described above. The three dimensional medical image 5 after the change may be any color if the color is distinguishable from the color of the additional information image. However, it is desirable for the contrast of the color of the additional information image with respect to the color of the three dimensional medical image 5 to be high. The contrast between the color of the three dimensional medical image 5 after the change in color and the color of the additional information image is at least higher than the contrast between the color of the three dimensional medical image 5 before the change in color and the color of the additional information image. That is, the color of the three dimensional medical image 5 is changed such that the relationship between the color of the additional information image and the color of the three dimensional medical image 5 after the change in color is more easily discriminated than the relationship between the color of the additional information image and the color of the three dimensional medical image 5 before the change in color.

In addition, the display control section ceases display of the additional information image, which is being displayed in color, and returns the color of the three dimensional medical image 5 from black and white display to color display, which was the manner of display prior to the change in color, when a command signal to not display the additional information image is input in a state in which the additional information image is being displayed.

The color change command receiving section 14 is configured to receive commands to change the color of the additional information image, and outputs signals indicating receipt of such commands to the display control section 12. The commands to change the color of the additional information image are input by a user using the input devices 4, and the color change command receiving section 14 receives signals input from the input devices 4. The commands to change the color of the additional information image may be input by displaying a palette, in which a plurality of colors are arranged, on the display 3, and by the user selecting a color from the palette.

When a command signal to change the color of the additional information image is input, the display control section 12 changes the color of the additional information image in accordance with the signal. In addition, the display control section 12 changes the color of the three dimensional medical image which is being displayed to a color that can be discriminated from the color of the additional information image after the change of color.

Specifically, in the case that the additional information image is displayed in color and the three dimensional medical image is displayed in black and white as described above, there is little effect even if the color of the additional information image is changed. However, in the case that the additional information image and the three dimensional medical image are displayed in different colors which are distinguishable from each other, there may be cases in which the color of the additional information image after the change in color is difficult to discriminate from the color of the three dimensional medical image.

Therefore, the display control section 12 changes the color of the three dimensional medical image to a color which can be discriminated from the color of the additional information image after the change in color when the color of the color of the additional information image is changed, in order to prevent such a problem from occurring.

It is desirable for the color of the three dimensional medical image at this time to be that which has a high contrast with the color of the additional information image which has been changed by the user. The color of the three dimensional medical image is changed such that the contrast between the color of the additional information image after the change in color and the color of the three dimensional medical image, which is also changed accompanying the change in color of the additional information image, is at least higher than the contrast between the color of the additional information image before the change in color and the color of the three dimensional medical image at that time in the same manner as described previously. That is, the color of the three dimensional medical image is changed such that the relationship between the color of the additional information image after the change in color and the color of the three dimensional medical image, which is also changed accompanying the change in color of the additional information image, is more easily discriminated than the relationship between the color of the additional information image before the change in color and the color of the three dimensional medical image at that time.

With respect to the change in color of the three dimensional medical image, it is possible for the display control section 12 to automatically determine such a color. The method for determining colors having high contrast may be the contrast determination method proposed by W3C. Alternatively, a table in which colors having high contrast are associated with each other may be set in the display control section 12, and the color of the three dimensional medical image may be determined and changed by referring to the table based on the color of the additional information image which is changed by the user.

Volume data which has been reconstructed based on slice data output from CT apparatuses and MRI apparatuses, volume data output from MS (MultiSlice) CT apparatuses and cone beam CT apparatuses, etc. are stored in the storage device 2 as the three dimensional medical image 5. Further, the CPR images 6, which are generated based on the volume data described above, are stored in the storage device 2.

Figure 2:
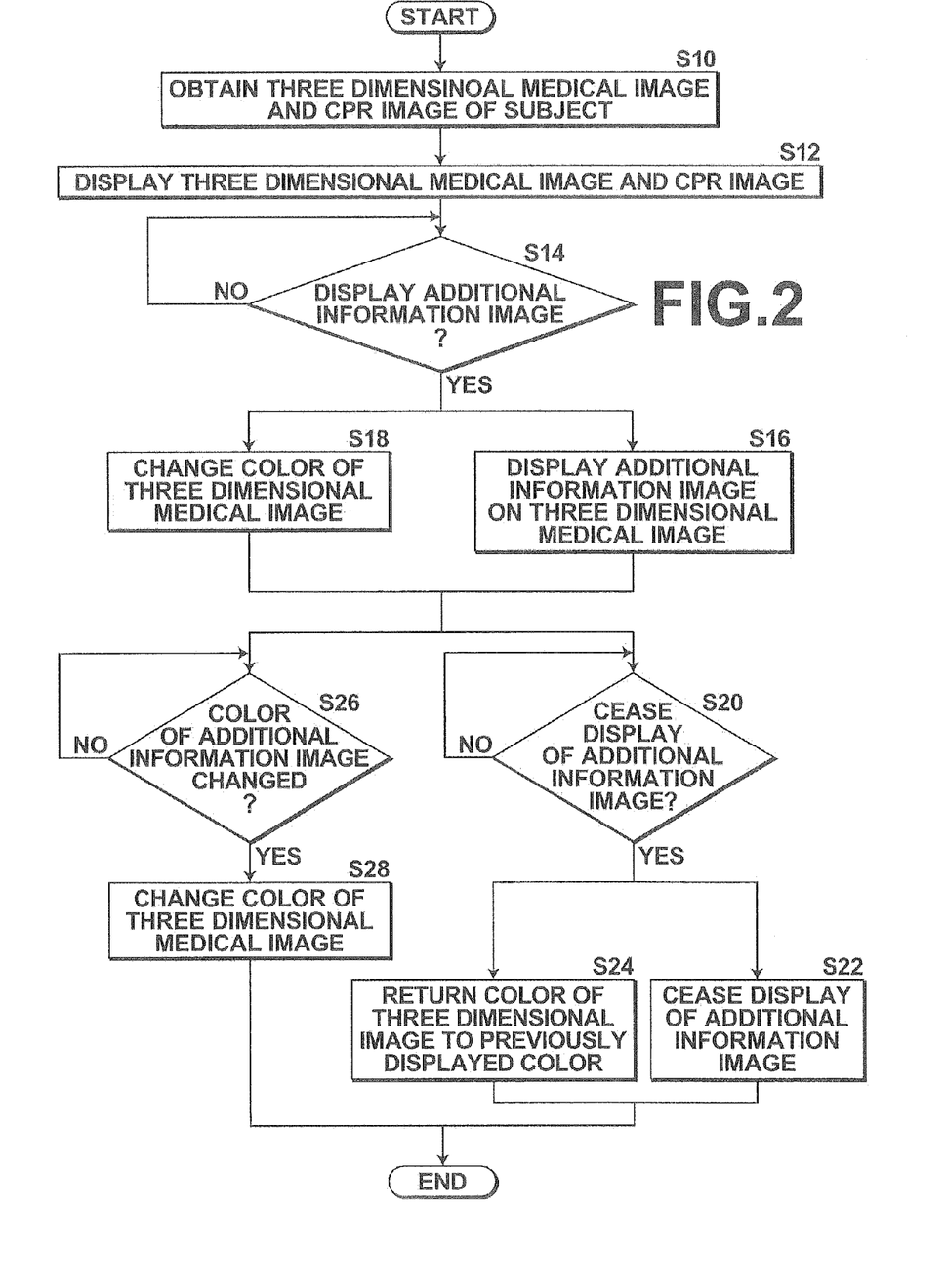
FIG. 2 is a flow chart that schematically illustrates the operations of the medical image display system in which the medical image display apparatus according to the embodiment of the present invention is incorporated.

FIG. 2 is a flowchart for explaining the operation of the medical image display system of the present embodiment. Hereinafter, a description will be given with reference to the flowchart. Note that here, a case will be described in which a surface image of the cut curved plane of a CPR image 6 is displayed as the additional information image.

First, in the medical image display system of the present embodiment, a list of the ID's of subjects is displayed on the display 3. Then, an ID of a subject is selected from the list of the ID's of subjects that is displayed on the display 3. When the selection operation by the user is detected by the medical image display apparatus 1, the three dimensional medical image 5 and the CPR image 6 related to the subject that is selected is obtained by the medical image obtaining section 11 of the medical image display apparatus 1 (S10).

Figure 3:
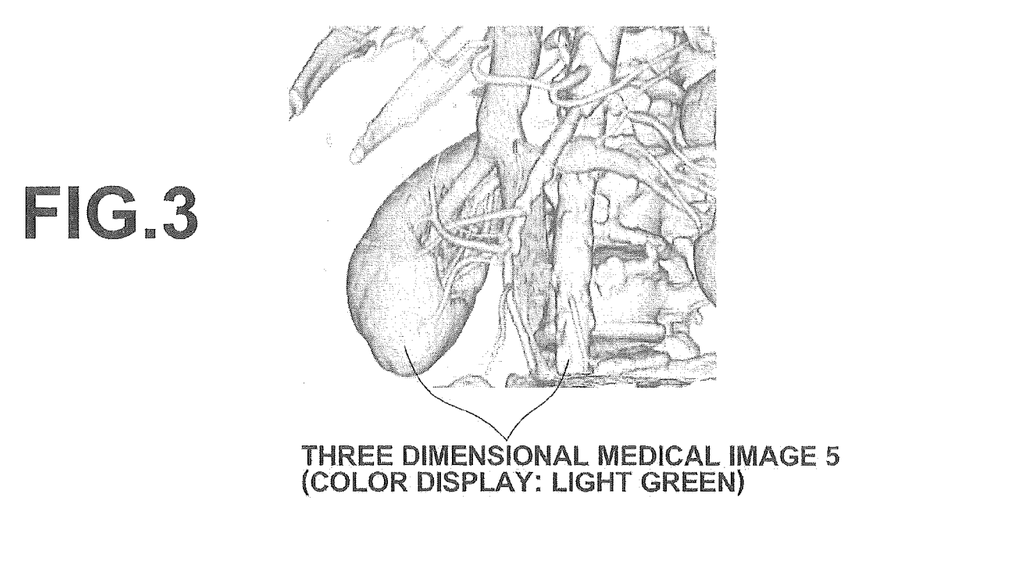
FIG. 3 is a diagram that illustrates an example of a three dimensional medical image.

Next, the three dimensional medical image 5 and the CPR image 6 obtained by the medical image obtaining section 11 are input to the display control section 12, and the display control section 12 displays the input three dimensional medical image 5 and CPR image 6 on the display 3 (S12). FIG. 3 is a diagram that illustrates an example of a three dimensional medical image 5, which is displayed on the display 3. The display control section 12 of the present embodiment displays the three dimensional medical image 5 in a light green color at this time.

Here, in the case that the user wishes to confirm the cut plane of the CPR image 6 within the three dimensional medical image 5 on the CPR image 6, the user employs the input devices 4 to input a command signal to display a surface image of the cut curved plane of the CPR image 6 as an additional information image (S14, YES).

The command signal input from the input devices 4 by the user is received by the additional information display command receiving section 13, and the additional information display command receiving section 13 outputs a signal indicating receipt of the command signal to the display control section 12.

Next, when the command signal to display the surface image of the cut curved plane is input, the display control section 12 displays the surface image of the cut curved plane in the three dimensional medical image 5 which is being displayed on the display 3 (S16).

Figure 4:
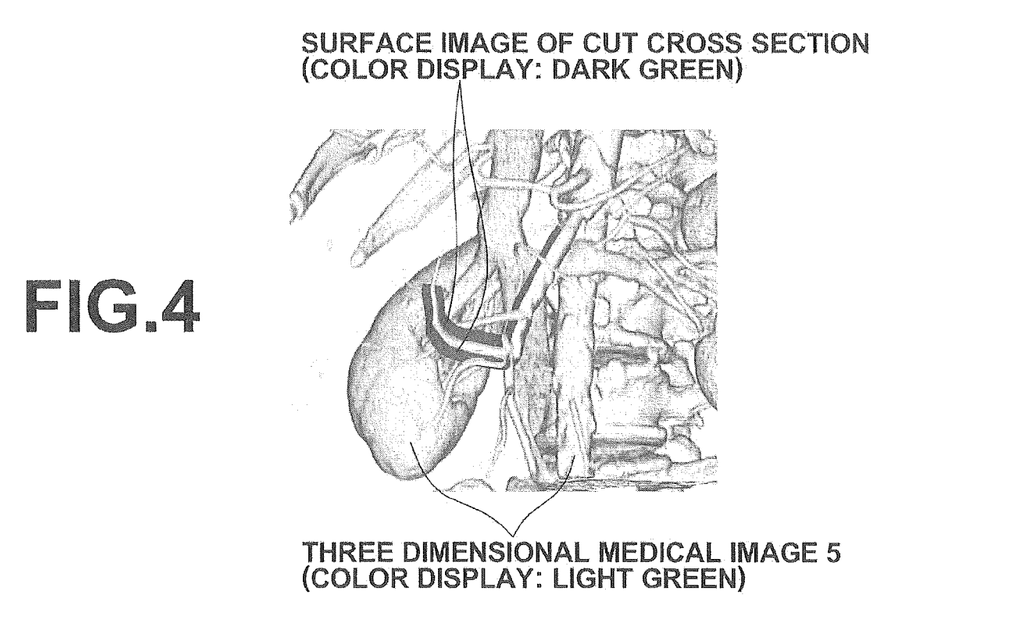
FIG. 4 is a diagram for explaining an example in which the color of a three dimensional medical image and the color of an image of the surface of a cut curved surface of a CPR image cannot be discriminated.

Here, for example, if the surface image of the cut curved plane is displayed in a dark green color while the three dimensional medical image 5 is displayed in a light green color as shown in FIG. 4, discrimination of the surface image of the cut curved plane and the three dimensional medical image 5 will be difficult.

Figure 5:
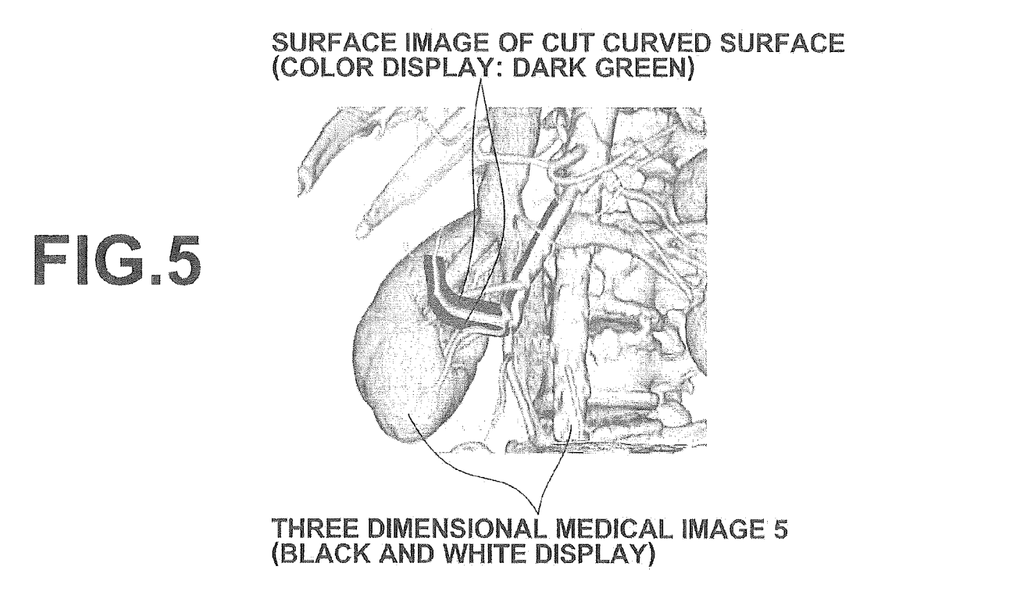
FIG. 5 is a diagram for explaining a case in which a three dimensional medical image is displayed in black and white and an image of the surface of a cut curved surface of a CPR image is displayed in color.

Therefore, when the command signal to display the surface image of the cut curved plane is input, the display control section 12 displays the surface image of the cut curved plane, and further changes the color of the three dimensional medical image 5 which is currently being to a color which is distinguishable from the color of the surface image of the curved surface (S18). More specifically, for example, the display of the three dimensional medical image 5 is changed from color display to black and white display as shown in FIG. 5. By changing the color of the three dimensional medical image 5 according to the color of the surface image of the cut curved plane in this manner, the surface image can be more easily discriminated within the three dimensional medical image 5, and the curved plane represented by the surface image can be more clearly recognized.

Then, if the user wishes to cease display of the surface image of the cut curved plane, the user inputs a command signal to not display the surface image of the cut curved plane using the input devices 4 (S20, YES).

The command signal input by the user via the input devices 4 is received by the additional information display command receiving section 13, and the additional information display command receiving section 13 outputs a signal indicating receipt of the command signal to the display control section 12.

Next, when the command signal to not display the surface image of the cut curved plane is input, the display control section 12 ceases display of the surface image of the cut curved plane on the display 3 (S22), and further returns the display of the three dimensional medical image 5 to display in the light green color, in which the three dimensional medical image 5 had been displayed before the changing of the color thereof (S24).

Meanwhile, if the user wishes to change the color of the surface image of the cut curved plane after the surface image of the cut curved plane is displayed in S16, the user inputs a command signal to change the color of the surface image of the cut curved plane using the input devices 4 (S26, YES).

The command signal to change the color input by the user via the input devices 4 is received by the color change command receiving section 14, and the color change command receiving section 14 outputs a signal indicating receipt of the command signal to the display control section 12.

Then, when the command signal to change the color is input, the display control section 12 changes the color of the surface image of the cut curved plane according to the signal, and further changes the color of the three dimensional medical image which is currently being displayed to a color that can be discriminated from the color of the surface image of the cut curved plane after the change in color thereof (S28).

However, in a state in which the surface image of the cut curved plane is displayed in a dark green color and three dimensional medical image is displayed in black and white as described above, and the color of the surface image of the cut curved plane is changed to a color different from dark green but is distinguishable from black and white display, it is possible to discriminate the black and white three dimensional medical image 5 and the surface image of the cut curved plane. Therefore, the color of the three dimensional medical image 5 is not changed in such a case.

On the other hand, if the color of the surface image of the cut curved plane is changed while in a state in which the surface image of the cut curved plane and the three dimensional medical image are displayed in different colors which are distinguishable from each other, the color of the three dimensional medical image is changed such that the surface image of the cut curved plane and the three dimensional medical image can be discriminated from each other after the change in color of the surface image of the cut curved plane.

The medical image display system of the embodiment is configured to receive a command to display an additional information image (surface image of the cut curved plane of a CPR image 6) along with a three dimensional medical image, and displays the additional information image along with the three dimensional medical image in the case that the command to display the additional information image is received. At this time, the color of the three dimensional image which is currently being displayed is changed to a color that can be discriminated from the color of the additional information image. Therefore, the additional information images can be displayed with a desired color, and the additional information images and the three dimensional medical images can be clearly distinguished from each other.

Figure 6:
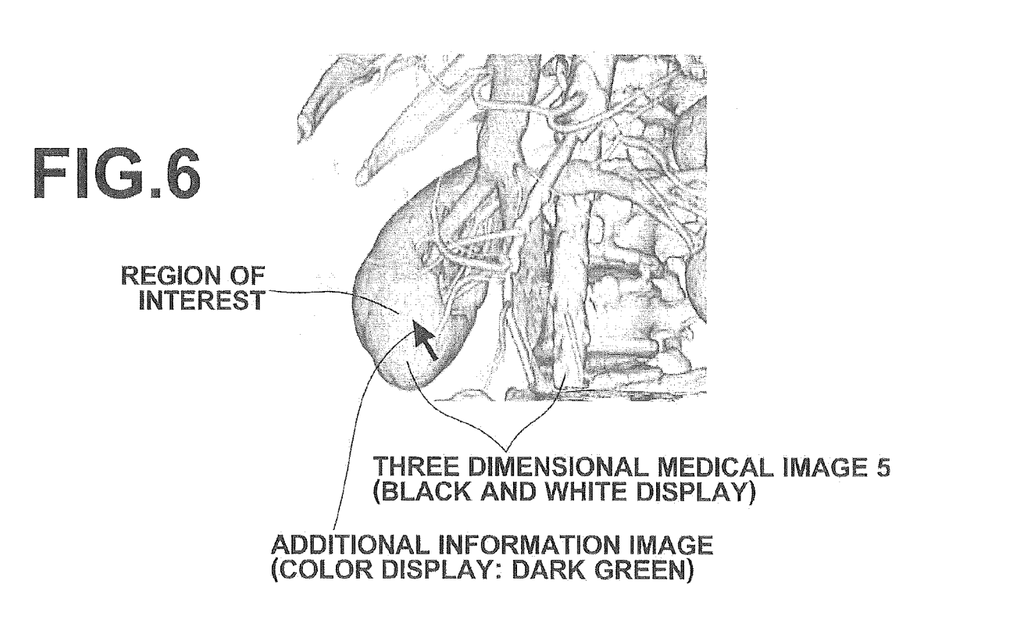
FIG. 6 is a diagram that illustrates an example of a case in which an arrow shaped cursor that indicates the position of a region of interest is displayed as an additional information image.
Figure 7:
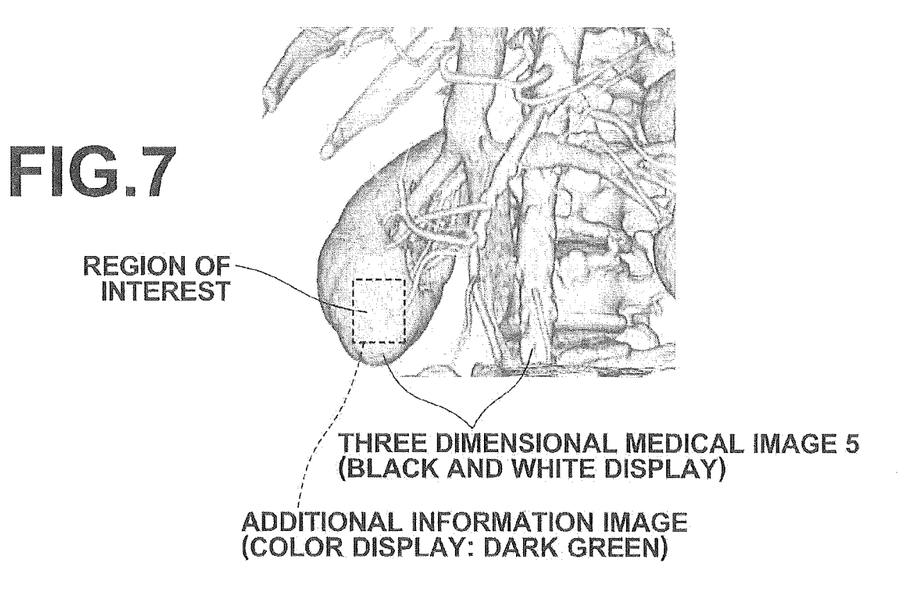
FIG. 7 is a diagram that illustrates an example of a case in which a frame that indicates the position and range of a region of interest is displayed as an additional information image.

In the above description, a case has been described in which the surface image of the cut curved plane of the CPR image 6 is displayed as the additional information image. However, the additional information image is not limited to such an image as described above. Examples of other types of additional information images include a cursor represented as an arrow that indicates the position of a region of interest, and a frame image that indicates the position and range of a region of interest. FIG. 6 is a diagram that illustrates an example of a case in which an arrow shaped cursor that indicates the position of a region of interest is displayed as an additional information image. FIG. 7 is a diagram that illustrates an example of a case in which a frame that indicates the position and range of a region of interest is displayed as an additional information image. When the arrow shaped cursor illustrated in FIG. 6 or the frame image illustrated in FIG. 7 are displayed as well, the color of the three dimensional medical image 5 may be changed to a color which can be discriminated from the color of the cursor and the color of the frame image in the same manner as that described above.

What is claimed is:

1. A medical image display apparatus, comprising:
    a medical image obtaining section for obtaining a three dimensional medical image of a subject;
    a display control section for displaying the three dimensional medical image obtained by the medical image obtaining section and an additional information image that represents information added to the three dimensional medical image; and
    an additional information display command receiving section for receiving a command to display as well as a command to not display the additional information image along with the three dimensional medical image, which is being displayed in color, the display control section displaying the additional information image in color along with the three dimensional medical image and changing a display of the displayed three dimensional medical image to a black and white display, when the command to display the additional information image is received in a state that the three dimensional medical image is being displayed in color, and ceasing display of the additional information image and returning the display of the three dimensional medical image to color display, when the command to not display the additional information is received in a state that the additional information image is being displayed in color.

2. A medical image display apparatus of claim 1, further comprising:
    a color change command receiving section for receiving a command to change the color of the additional information image,
    wherein the display control section further changes the color of the displayed three dimensional image to the color which can be discriminated from the color of the additional information image after the color of the additional information image is changed, in response to receipt of the command to change the color of the additional information image.

3. A medical image display apparatus as defined in claim 2, wherein the display control section displays an indicator that indicates a predetermined position within the three dimensional medical image as the additional information image.

4. A medical image display apparatus as defined in claim 2, wherein the display control section displays a Curved Planar Reformation (CPR) image based on the three dimensional medical image, and displays an image that represents a cut curved surface of the CPR image as the additional information image on the three dimensional medical image.

5. A medical image display apparatus as defined in claim 2, wherein:
    the additional information display command receiving section also receives a command to not display the additional information image; and
    the display control section ceases display of the additional information image and returns the color of the three dimensional medical image to the color it had been displayed in prior to being changed, when the command to not display the additional information image is received.

6. A medical image display apparatus as defined in claim 5, wherein:
the display control section returns the display of the three dimensional medical image to color display, which is a manner in which the three dimensional medical image is displayed prior to being changed to black and white display, when the command to not display the additional information image is received.

7. A medical image display apparatus as defined in claim 2, wherein the display control section displays a volume rendered image as the three dimensional medical image.

8. A medical image display apparatus as defined in claim 1, wherein the display control section displays an indicator that indicates a predetermined position within the three dimensional medical image as the additional information image.

9. A medical image display apparatus as defined in claim 1, wherein the display control section displays a Curved Planar Reformation (CPR) image based on the three dimensional medical image, and displays an image that represents a cut curved surface of the CPR image as the additional information image on the three dimensional medical image.

10. A medical image display apparatus as defined in claim 1, wherein:
the additional information display command receiving section also receives a command to not display the additional information image; and
the display control section ceases display of the additional information image and returns the color of the three dimensional medical image to the color it had been displayed in prior to being changed, when the command to not display the additional information image is received.

11. A medical image display apparatus as defined in claim 1, wherein the display control section displays a volume rendered image as the three dimensional medical image.

12. A medical image display method comprising:
obtaining a three dimensional medical image of a subject; and
displaying the three dimensional medical image and an additional information image that represents information added to the three dimensional medical image which is being displayed in color, wherein:
in the case that the additional information image is displayed in color along with the three dimensional medical image and a display of the displayed three dimensional medical image is changed to a black and white display, when a command to display as well as a command to not display the additional information image is received in a state that the three dimensional medical image is being displayed in color, and ceasing display of the additional information image and returning the display of the three dimensional medical image to color display, when the command to not display the additional information is received in a state that the additional information image is being displayed in color; and
displaying the additional information image in color.

13. A medical image display method of claim 12, further comprising:
receiving a command to change the color of the additional information image; and
further changing the color of the displayed three dimensional image to the color which can be discriminated from the color of the additional information image after the color of the additional information image is changed, in response to receipt of a command to change the color of the additional information image.

14. A non-transitory computer readable medium having a medical image display program stored therein, the medical image display program causing a computer to function as:
a medical image obtaining section for obtaining a three dimensional medical image of a subject;
a display control section for displaying the three dimensional medical image obtained by the medical image obtaining section and an additional information image that represents information added to the three dimensional medical image; and
an additional information display command receiving section for receiving a command to display as well as a command to not display the additional information image along with the three dimensional medical image, which is being displayed in color, the display control section displaying the additional information image in color along with the three dimensional medical image and changing a display of the displayed three dimensional medical image to a black and white display, when the command to display the additional information image is received in a state that the three dimensional medical image is being displayed in color, and ceasing display of the additional information image and returning the display of the three dimensional medical image to color display, when the command to not display the additional information is received in a state that the additional information image is being displayed in color.

15. A non-transitory computer readable medium of claim 14, further comprising
a color change command receiving section for receiving a command to change the color of the additional information image,
wherein the display control section further changes the color of the displayed three dimensional image to the color which can be discriminated from the color of the additional information image after the color of the additional information image is changed, in response to receipt of a command to change the color of the additional information image.

* * * * *